US010413665B2

(12) United States Patent
Rioux et al.

(10) Patent No.: US 10,413,665 B2
(45) Date of Patent: Sep. 17, 2019

(54) WEARABLE MEDICATION DELIVERY DEVICE

(71) Applicant: Insulet Corporation, Acton, MA (US)

(72) Inventors: Robert Rioux, Ashland, MA (US); David Nazzaro, Groveland, MA (US)

(73) Assignee: Insulet Corporation, Acton, MA (US)

( * ) Notice: Subject to any disclaimer, the term of this patent is extended or adjusted under 35 U.S.C. 154(b) by 0 days.

(21) Appl. No.: 15/358,945

(22) Filed: Nov. 22, 2016

(65) Prior Publication Data

US 2017/0143900 A1 May 25, 2017

Related U.S. Application Data

(60) Provisional application No. 62/259,706, filed on Nov. 25, 2015.

(51) Int. Cl.
*A61M 5/172* (2006.01)
*A61M 5/142* (2006.01)
(Continued)

(52) U.S. Cl.
CPC ...... *A61M 5/1723* (2013.01); *A61M 5/14216* (2013.01); *A61M 5/14526* (2013.01);
(Continued)

(58) Field of Classification Search
CPC .... A61M 2205/3569; A61M 2205/581; A61M 2205/582; A61M 2205/583;
(Continued)

(56) References Cited

U.S. PATENT DOCUMENTS 3,631,847 A  1/1972 Hobbs
4,781,688 A  11/1988 Thoma et al.
(Continued)

FOREIGN PATENT DOCUMENTS

EP  0341049 A2  11/1989
EP  0496305 A2  7/1992
(Continued)

OTHER PUBLICATIONS

International Search Report and Written Opinion of PCT/US2018/018901, dated Jun. 8, 2018, 12 pages.
(Continued)

*Primary Examiner* — Emily L Schmidt (57) ABSTRACT

Systems and methods for delivering a medication to a person experiencing an emergency medical event without requiring intervention or action on the part of the person. A device encases a reservoir of medication and a delivery mechanism. Sensors in the housing sense a physical attribute of the person and circuitry monitors information collected by the sensors to determine if the person is experiencing a severe medical condition or event based on the information. An input device on or in the housing, such as a button, may be used or activated by the person if the detected condition or event is a false positive to cancel further action. If the system does not include the button or if the user does not press it in time, the system activates the delivery device and injects the medication into the person.

20 Claims, 8 Drawing Sheets

(51) Int. Cl.
*A61M 5/145* (2006.01)
*A61M 5/158* (2006.01)

(52) U.S. Cl.
CPC ............ *A61M 5/158* (2013.01); *A61M 5/172* (2013.01); *A61M 2005/1585* (2013.01); *A61M 2005/1586* (2013.01); *A61M 2205/18* (2013.01); *A61M 2205/276* (2013.01); *A61M 2205/3368* (2013.01); *A61M 2205/3569* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/8206* (2013.01); *A61M 2230/06* (2013.01); *A61M 2230/20* (2013.01); *A61M 2230/201* (2013.01); *A61M 2230/30* (2013.01); *A61M 2230/50* (2013.01); *A61M 2230/63* (2013.01)

(58) Field of Classification Search
CPC ...... A61M 2005/1585; A61M 2230/63; A61M 5/14248; A61M 2005/14268
See application file for complete search history.

(56) References Cited

U.S. PATENT DOCUMENTS

| | | | |
|---|---|---|---|
| 4,994,047 | A | 2/1991 | Walker et al. |
| 4,994,947 | A | 2/1991 | Fesko |
| 5,505,709 | A | 4/1996 | Funderburk et al. |
| 5,584,813 | A | 12/1996 | Livingston et al. |
| 5,741,228 | A | 4/1998 | Lambrecht et al. |
| 5,800,405 | A | 9/1998 | McPhee |
| 5,851,197 | A | 12/1998 | Marano et al. |
| 5,865,806 | A | 2/1999 | Howell |
| 5,871,470 | A | 2/1999 | McWha |
| 6,090,092 | A | 7/2000 | Fowles et al. |
| 6,475,196 | B1 | 11/2002 | Vachon |
| 6,569,125 | B2 | 5/2003 | Jepson et al. |
| 6,572,542 | B1 | 6/2003 | Houben et al. |
| 7,008,404 | B2 | 3/2006 | Nakajima |
| 2002/0123740 | A1 | 9/2002 | Flaherty et al. |
| 2005/0020980 | A1 | 1/2005 | Inoue et al. |
| 2005/0203461 | A1* | 9/2005 | Flaherty ............ A61M 5/14248 604/131 |
| 2006/0204535 | A1 | 9/2006 | Johnson |
| 2007/0129690 | A1 | 6/2007 | Rosenblatt et al. |
| 2008/0065050 | A1 | 3/2008 | Sparks et al. |
| 2009/0069787 | A1* | 3/2009 | Estes ................... A61M 5/1413 604/503 |
| 2009/0099521 | A1 | 4/2009 | Gravesen et al. |
| 2011/0054390 | A1 | 3/2011 | Searle et al. |
| 2011/0144586 | A1* | 6/2011 | Michaud ............ A61M 5/1413 604/151 |
| 2011/0251509 | A1 | 10/2011 | Beyhan et al. |
| 2012/0010594 | A1* | 1/2012 | Holt .................. A61M 5/14248 604/506 |
| 2013/0060233 | A1 | 3/2013 | O'Connor et al. |
| 2013/0178791 | A1 | 7/2013 | Javitt |
| 2014/0316379 | A1 | 10/2014 | Sonderegger et al. |

FOREIGN PATENT DOCUMENTS

| | | |
|---|---|---|
| WO | 9800193 A1 | 1/1998 |
| WO | 0030705 A1 | 6/2000 |
| WO | 2001072354 A2 | 10/2001 |
| WO | 2002015954 A1 | 2/2002 |
| WO | 2006053007 A2 | 5/2006 |
| WO | 2007064835 A2 | 6/2007 |
| WO | 2008024810 A2 | 2/2008 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2013078200 A1 | 5/2013 |
| WO | 2013182321 A1 | 12/2013 |
| WO | 2014194183 A2 | 12/2014 |
| WO | 2015061493 A1 | 4/2015 |
| WO | 2015081337 A2 | 6/2015 |
| WO | 2016141082 A1 | 9/2016 |
| WO | 2017205816 A1 | 11/2017 |

OTHER PUBLICATIONS

International Search Report and Written Opinion for Application No. PCT/US2018/052464, dated Jan. 4, 2019, 14 pages.

\* cited by examiner

```
┌─────────────────────────────────────────┐
│ Receive input from a sensor representing│
│ position/velocity/acceleration/jerk of a│
│                 person                  │
│                                     602 │
└─────────────────────────────────────────┘
                    │
                    ▼
┌─────────────────────────────────────────┐
│ Computationally determine that the person│
│         is experiencing a seizure        │
│                                     604 │
└─────────────────────────────────────────┘
                    │
                    ▼
┌─────────────────────────────────────────┐
│  Optionally prompt person to identify   │
│            false positive                │
│                                     606 │
└─────────────────────────────────────────┘
                    │
                    ▼
┌─────────────────────────────────────────┐
│    Trigger actuation of medication      │
│                delivery                  │
│                                     608 │
└─────────────────────────────────────────┘
```

WEARABLE MEDICATION DELIVERY DEVICE

CROSS-REFERENCE TO RELATED APPLICATIONS

This application claims priority to U.S. Provisional Patent Application No. 62/259,706, filed Nov. 25, 2015, the entirety of which is hereby incorporated by reference.

TECHNICAL FIELD

Embodiments herein generally relate to medication delivery and, more particularly, to wearable medication delivery devices for providing medication to a user experiencing a severe medical event.

BACKGROUND

Some medical situations require rapid delivery of a medication to a person to avoid death or serious injury. For example, if a person is exposed to a chemical warfare agent, such as sarin gas, the person may require the administration of an antidote such as atropine within a very short period of time. Similarly, for someone having a bee-sting allergy, epinephrine must be administered soon after a bee sting occurs. Other such medical conditions or events that may require urgent attention can include episodes caused by food allergies or epileptic attacks. Often, there is not enough time to transport the afflicted person to a care facility or even to bring a medical professional to the person.

As a result, people required to be in zones in which chemical warfare is a possibility, such as soldiers, and people who are known to have medical conditions such as allergic reactions to substances or events such as bee stings or foods are encouraged to carry self-injector devices that permit the quick delivery of a needed medication. These devices are typically about five inches long, cylindrical, and resemble a large pen or magic marker. The user holds one end of the self-injector on an injection site (e.g., the thigh of a leg) and a predetermined amount of medication is automatically injected. One such device is sold under the trade name EPIPEN.

Use of these devices presents a number of drawbacks, however. The user is required to know both how to operate the device and when to operate the device. Improper operation may result in little or no medication actually injected and improper timing may result in injection occurring too late. Furthermore, the user must be conscious and capable of performing the self-injection. Because some chemical agents and allergic reactions cause seizures, the user may be incapable of performing the self-injection due to seizing before the person even realizes that an attack or allergen exposure has occurred. A need therefore exists for a system and method to deliver antidotes and other medication even if or when a user is incapable of doing so.

BRIEF DESCRIPTION OF THE DRAWINGS

In the drawings, like reference characters generally refer to the same parts throughout the different views. In the following description, various embodiments of the present invention are described with reference to the following drawings, in which.

DETAILED DESCRIPTION

Various embodiments described herein include systems and methods for delivering a medication to a person exposed or subjected to an emergency medical event without requiring intervention or action on the part of the person. The event may be a chemical-weapon attack, bee sting, allergic reaction, epileptic attack, or any other event. In some embodiments, a pod or housing encases a reservoir of medication and a delivery device, such as a hypodermic needle. The housing is held in contact with or in close proximity to a body part of a person, such as the person's thigh, via an adhesive, strap, pouch, or any similar means. Sensors in the housing, such as motion sensors, accelerometers, biosensors, or any other type of sensor, sense a physical attribute of the person, such as the motion and/or biochemistry of the person, and a computer processor (and associated circuitry) monitor information collected by the sensors and determine if the person is experiencing a medical event, such as a seizure or allergic attack, based on the information. The housing may further include an output communications device, such as a loudspeaker, vibration generator, thermal indicator, or electric-shock dispenser, that signals to the person that a seizure or other severe medical condition or events has been detected. An input device on or in the housing, such as a button, may be used or activated by the person in response to the signal if the detected condition or event is a false positive to cancel further action. If the system does not include the button or if the user does not press it in time, the system activates the delivery device and injects the medication into the person.

Figure 1:
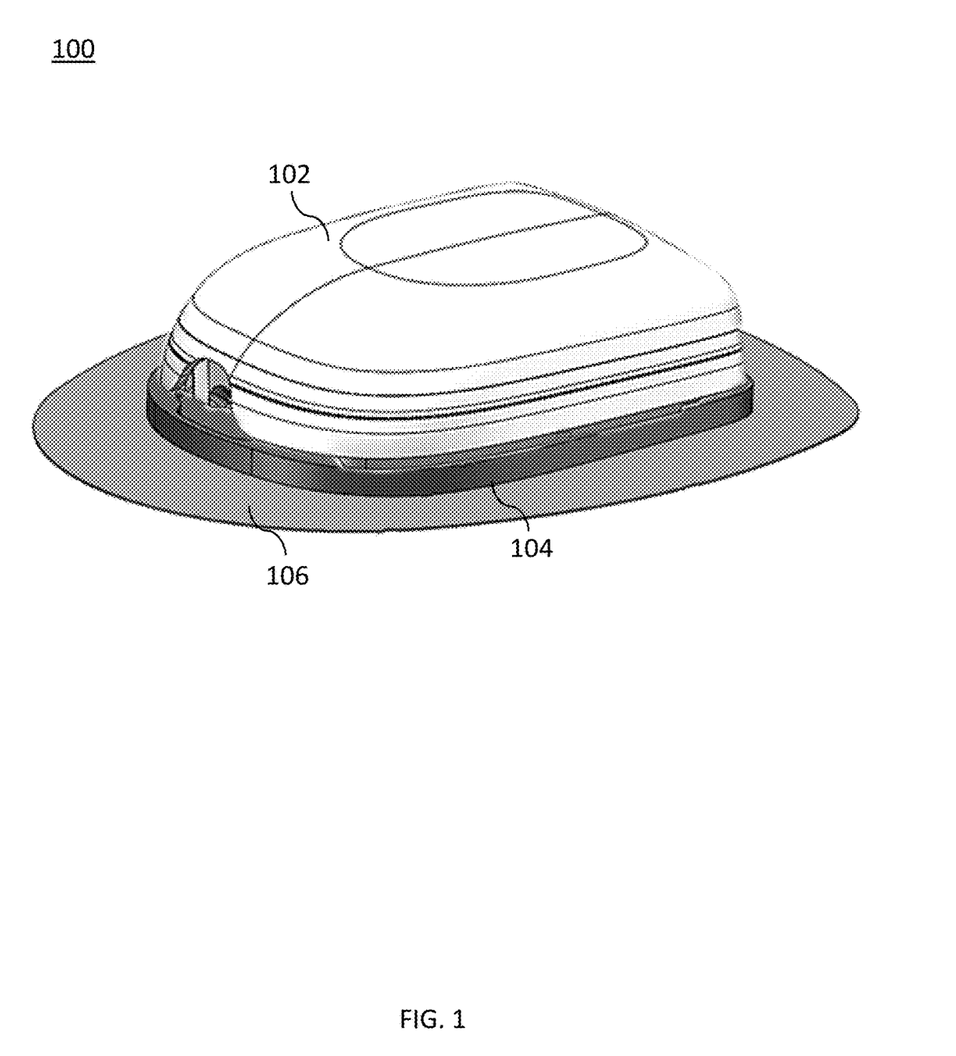
FIG. 1 illustrates a first exemplary wearable device for delivering medication.

FIG. 1 illustrates a wearable device 100 for delivering medication to a wearer or user of the wearable device 100. A housing 102 may be used to enclose a hypodermic needle, needle actuator, medication reservoir, motion sensor, medical condition sensor, environmental sensor, computer processor, and/or other elements, components, or devices described herein. The housing 102 may be made of metal, plastic, or any other material or any combination thereof. In some embodiments, the housing 102 can include a detachable portion 104 that includes one or more enclosed components, as described in greater detail below. The housing 102 may further, in some embodiments, be attached on one side to an adhesive member 106 that facilitates attachment to a person's body. The adhesive member 106 may be made of one or more flexible materials such as gauze, fabric, rubber, latex, or any other material, which may be arranged in one or more layers. An adhesive substance may be disposed on one side of the adhesive member 106. A person may, for example, first remove a non-adhesive layer affixed to the adhesive substance to thereby expose the adhesive substance and then adhere the adhesive member 106 to his or her body. In other embodiments, the housing 102 can be held in place touching or adjacent to a person's body via use of a strap, pouch, or similar means, and the adhesive member 106 may not be present or needed.

Figure 2A:
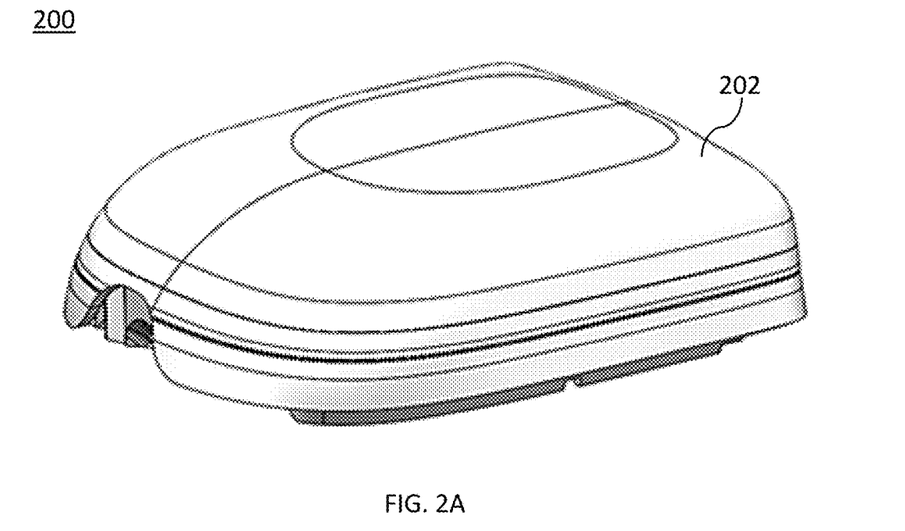
FIGS. 2A and 2B illustrate a second exemplary wearable device for delivering medication.
Figure 2B:
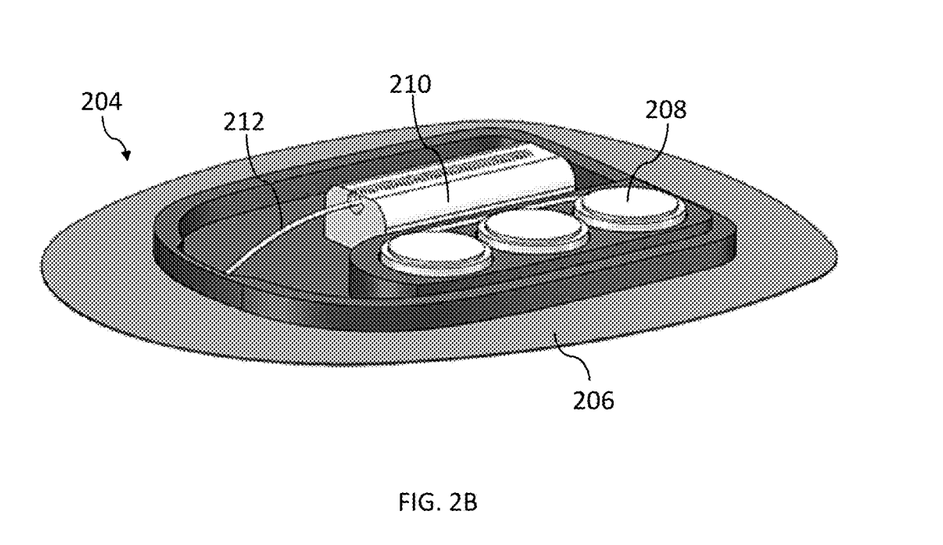

FIGS. 2A and 2B illustrate a wearable device 200 configured in two parts. The wearable device 200 can represent a particular implementation of the wearable device 100 of FIG. 1. The wearable device 200 can include a first portion 202 (shown in FIG. 2A) and a second portion 204 (shown in FIG. 2B). The first portion 202 can include a number of components such as, for example, a motion sensor and a computer processor. In various embodiments, the first portion 202 can further include a medical condition sensor and/or an environmental sensor. The second portion 204 can include an adhesive member 206, batteries 208, a needle unit 210, and a needle 212. The adhesive member 206 can represent an implementation of the adhesive member 106 depicted in FIG. 1. In some embodiments, however, the first portion 202 can be a cover to protect the components disposed in the second portion 204 and does not itself house any components. The components may be apportioned such that one portion (e.g., the first portion 202) is re-usable, while some or all of the perishable components (e.g., the medication and batteries) are in the second portion 204. The person using the system may therefore need to replace only the second portion 204 upon expiration of the medication and/or battery.

The first and second portions 202 and 204 may be configured to releasably attach to each other, as shown in FIG. 2. The first and second portions 202 and 204 may be held in place together by friction (e.g., friction fit), by tabs, by screws, or by any other means of attachment. In some embodiments, the first and second portions 202 and 204 are configured to allow any person to separate them. In other embodiments, the first and second portions 202 and 204 are configured to allow only qualified persons (e.g., medical professionals) to separate them by using, for example, a locking mechanism, screws or bolts with specially-shaped heads, or similar means. In some embodiments, the first and second portions 202 and 204 include a sticker, thread, or similar tell-tale that indicates whether the first and second portions 202 and 204 have been separated by snapping, breaking, or moving (e.g., one or more of the first and second portions 202 and 204 may include a tamper evident device or mechanism indicating when the first and second portions 202 and 204 have been separated). The first and second portions 202 and 204 may further include a self-destruct or disabling mechanism that can be triggered if the first and second portions 202 and 204 are separated or separated improperly.

The batteries 208 may be used to provide power to the needle unit 210 and may be AA or AAA cell batteries, watch batteries, rechargeable batteries, or any other type or number of batteries (including a single cell battery). In some embodiments, the batteries 208 also or instead provide power to components within the first portion 202. For example, the first portion 202 may have conducting metal elements that mate with corresponding metal elements in the second portion 204 when the first and second portions 202 and 204 are attached to each other, thereby enabling power from the batteries 208 to be provided to components in the first portion 202. The first portion 202 may also or instead have conducting metal elements that contact the batteries 208 themselves (e.g., directly) to thereby supply power to components therein. In other embodiments, the first portion 202 includes another power supply (e.g., one or more additional batteries).

The first and second portions 202 and 204 may similarly have data or signal connectors that form a data or signal path when the first and second portions 202 and 204 are attached together to thereby permit the transmission of data or signals there between. For example, the first portion 202 may have a connector with pins that mates with a socket on the second portion 204 when the first and second portions 202 and 204 are attached to each other. This data or signal path may be used to, for example, communicate between a processor disposed in the first portion 202 and the needle unit 210 in the second portion 204.

The needle unit 210 may include a fluid reservoir for storing and/or dispensing a quantity of liquid medication or drug. In some embodiments, the fluid reservoir can be a cylinder or similar shape having a cross-sectional shape of a circle, oval, rectangle, square, or any other shape. In these embodiments, the needle 212 can be fluidly connected to one end of the cylinder, and a plunger can be disposed at the other end of the cylinder. The medicine or drug may be dispensed through the needle 212 via mechanical or electro-mechanical means, such as an electric motor that turns a gear that advances the plunger. The plunger may alternatively be driven by electrochemical means, such as by causing the creation or expansion of a gas by applying an electric current to a substance to thereby exert a force on the plunger. In other embodiments, the fluid reservoir can exert a force on the liquid medicine disposed therein. For example, one or more inner walls of the fluid reservoir may include an elastic member that is stretched such that it exerts a force on the liquid (e.g., an elastic bladder). A propellant may alternatively be added to the fluid reservoir to exert force on the liquid. In these embodiments, instead of or in addition to a plunger, the needle unit 210 can include a valve that, once open, permits the liquid under pressure to exit the fluid reservoir and travel through the needle 212.

Figure 3A:
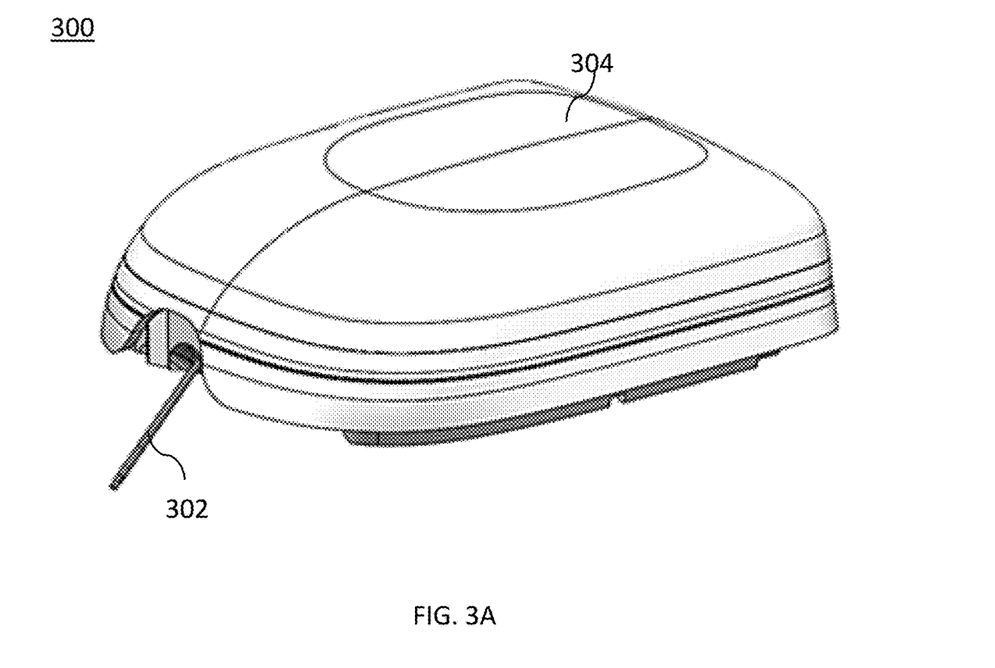
FIGS. 3A and 3B illustrate a third exemplary wearable device for delivering medication.
Figure 3B:
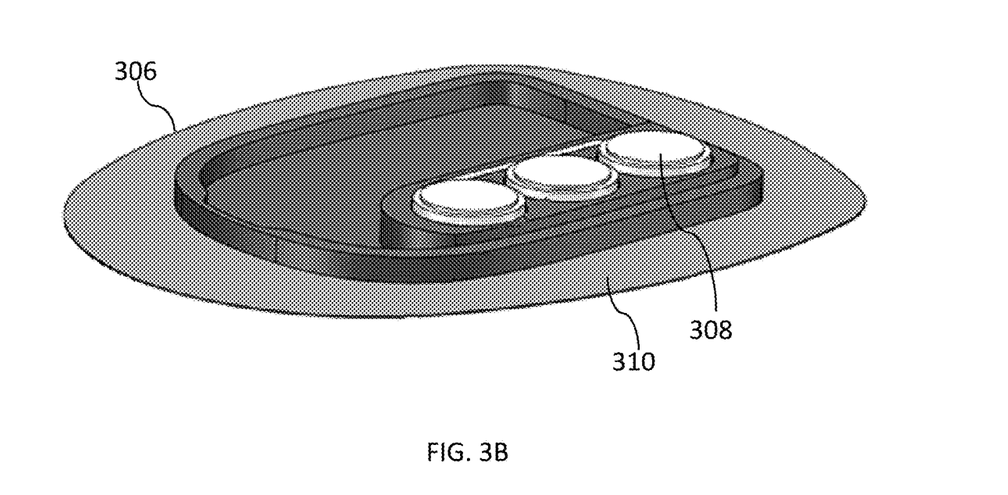

FIGS. 3A and 3B illustrate a wearable device 300. The wearable device 300 can represent another embodiment of a medication delivery device of the present invention. In this embodiment, as shown in FIG. 3A, a needle 302 can be part of a first portion 304 of the wearable device 300 (as opposed to being part of the second portion 204 as shown in the embodiment of FIG. 2B). A second portion 306 of the wearable device 300 can include batteries 308 and an adhesive member 310. The present invention is not limited to any particular division of components between the two portions 302 and 306 as any division or placement of any constituent components is within the scope of the wearable devices described. In addition, other embodiments of the present invention can include additional portions (e.g., more than two portions) or fewer portions (e.g., a single portion such that the housing/entire wearable device is provided as a single piece).

Figure 4A:
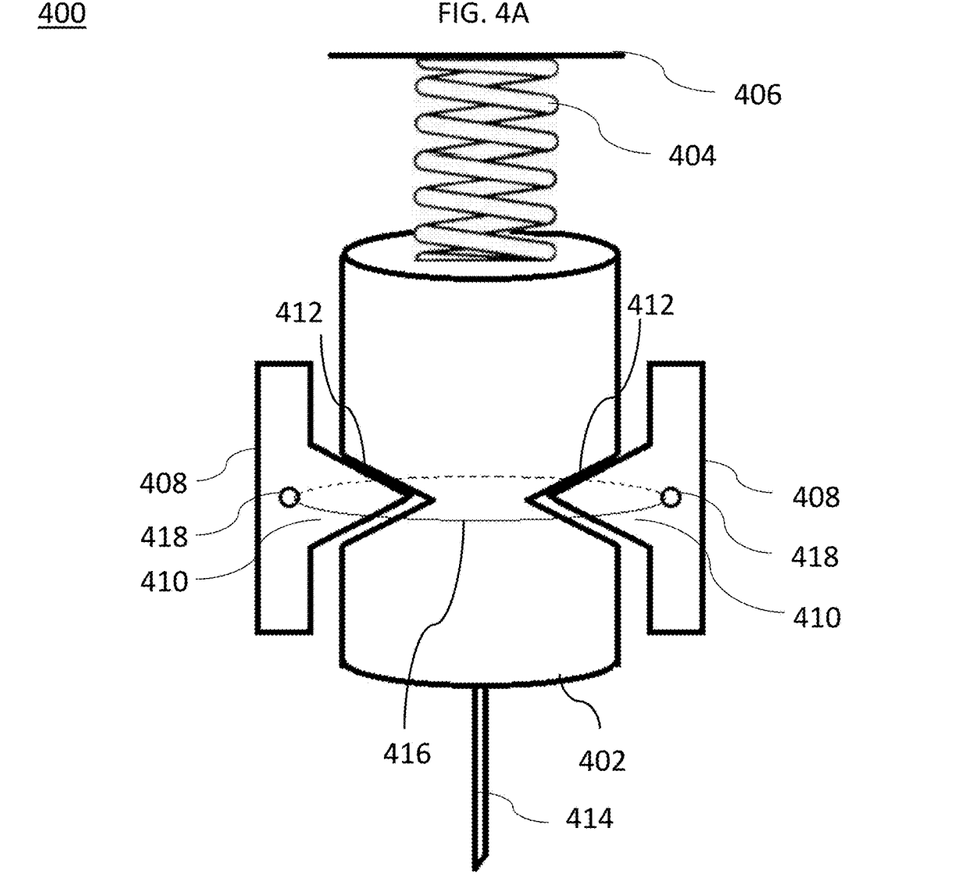
FIGS. 4A and 4B illustrate first and second views of a first exemplary needle deployment system.
Figure 4B:
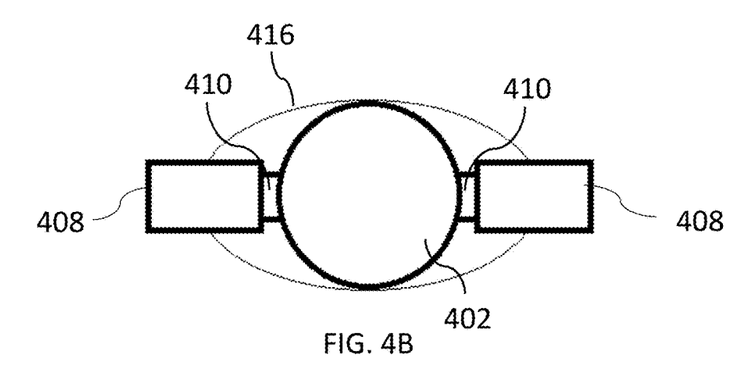

FIGS. 4A and 4B illustrate top and side views, respectively, of an exemplary system 400 for deploying a needle disposed within a wearable device of the present invention (such as one of the wearable devices 100, 200, or 300) into the body of a person for subsequent dispensing of a medication or drug there through. In this embodiment, a needle driver 402 is under load of a spring 404 that is compressed between the needle driver 402 and another surface 406. The surface 406 may be part of a housing, attached to a housing, or may be any other surface of a wearable device as described herein. One or more keys 408 can hold the needle driver 402 in place and prevent the spring 404 from expanding to propel the needle driver 402 forward. Protrusions 410 in the keys 408 can mate with corresponding notches 412 in the needle driver 402. The needle driver 402, the spring 404, the surface 406, and the keys 408 may be constructed using any material, such as metal or plastic. The needle driver 402 may be a medication reservoir or act as a fluid conduit between a separate medication reservoir and the needle.

The keys 408 may be moved to thereby release the needle driver 402 and allow the spring 404 to move it, thereby propelling a needle 414 attached to the needle driver 402 forward in response to a signal. Additional support members may be included to guide the needle driver 402 and/or keys 408 such that they move only in one dimension or direction (or otherwise restrict the movement of the needle driver 402 and/or keys 408). As explained in greater detail below, an actuation signal may be generated by a processor that, in response to data collected by a sensor (such as a motion sensor or biosensor), determines that the person wearing the device is experiencing a medical event such as a seizure or allergic attack. In various embodiments, an electrically deformable material 416, such as shape-memory wire made from, for example, copper-aluminum-nickel or nickel-titanium alloys, can be disposed around the needle driver 402 and through holes 418 in the one or more keys 408. Any other type of electrically deformable material, such as magnetic-shape memory, piezoelectric materials, or shape-memory polymer, is within the scope of the present invention. When the signal to release the keys 408 is received, an electric current can be provided to run through electrically deformable material 416, thereby causing it to change shape. For example, the diameter of the electrically deformable material 416 may increase when the current is applied, thereby causing the keys 408 to move away from the needle driver 402 such that the protrusions 410 no longer mate with the notches 412. In other embodiments, the electrically deformable material 416 may be configured to decrease in length when current is applied. In these embodiments, the electrically deformable material 416 can be positioned to pull the keys 408 away from the needle driver 402 to thereby release it. Any configuration of electrically deformable material and keys is within the scope of the present invention as will be understood by one of skill in the art. Further, any other system and method of mechanically actuating a needle to extend into the body of the person in response to a received electric or electronic signal is similarly within the scope of the present invention.

Figure 4C:
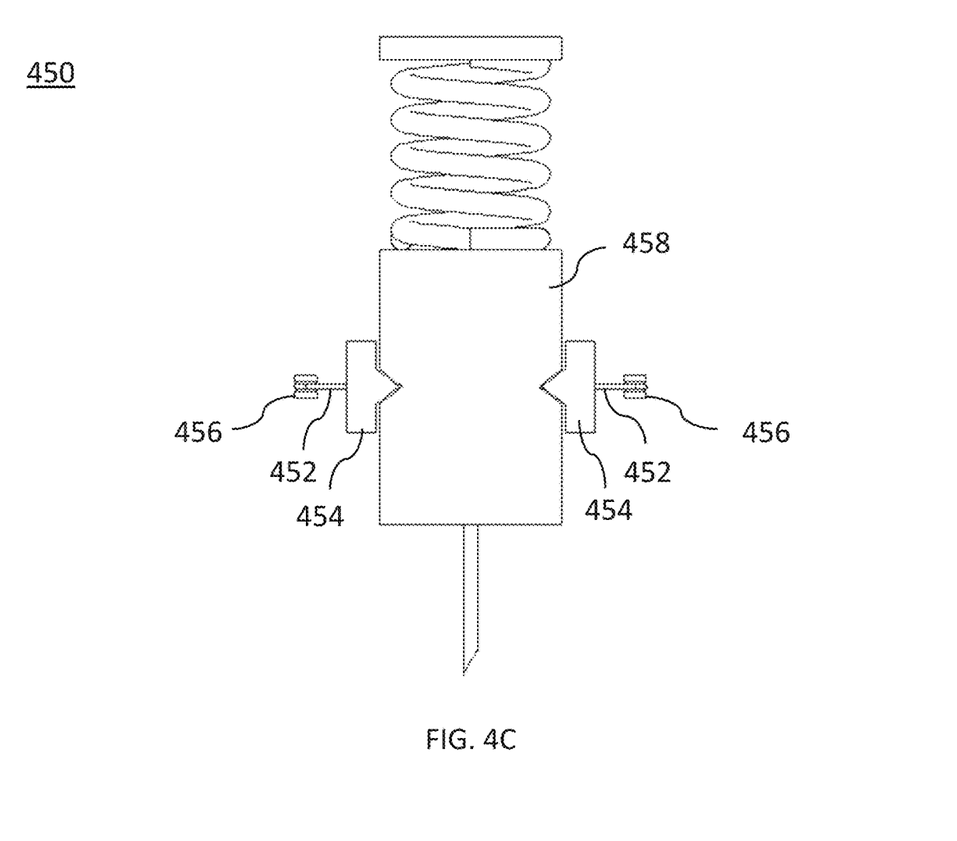
FIGS. 4C and 4D illustrate first and second views of a second exemplary needle deployment system.
Figure 4D:
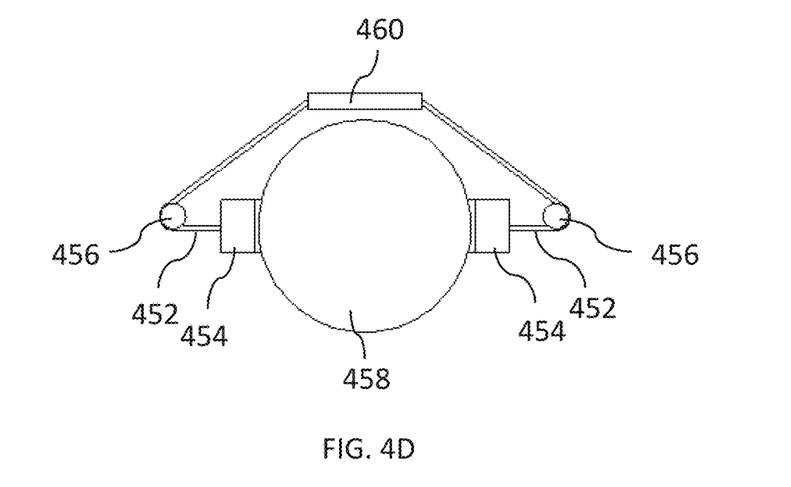

FIGS. 4C and 4D illustrate top and side views, respectively, of a second exemplary system 450 for deploying a needle disposed within a wearable device of the present invention (such as one of the wearable devices 100, 200, or 300) into the body of a person for subsequent dispensing of a medication or drug there through. In this embodiment, an electrically deformable material 452 can be connected to keys 454 and can run over pulleys 456. When the electrically deformable material 452 is shortened (e.g., in response to an actuation signal), the electrically deformable material 452 can exert a force on each key 454 in a radial outward direction with respect to needle driver 458. By doing so, the keys 454 can be moved away from the needle driver, thereby no longer restricting movement of the needle drive 458. As a result, the needle driver can move as described above in relation to needle driver 402. As shown in FIG. 4D, a hook 460 may be used to connect the electrically deformable material 452 to a power source. The hook 460 may also be used to anchor the electrically deformable material 452 such that, when power is applied to the electrically deformable material 452, both of the keys 454 separate away from the needle driver 458. If, for example, the electrically deformable material 452 were unanchored and if one key 454 were subject to a greater frictional force with respect to the needle driver 408 than the other key 454, contracting the electrically deformable material 452 might move only one key 454, and the needle driver 408 might not be free to move. In other embodiments, separate, unconnected electrically deformable materials 452 can be provided for each key 454. The systems 400 and 450 depicted in relation to FIGS. 4A-4D can include any number of keys (e.g., as few as a single key or two or more keys).

Figure 5:
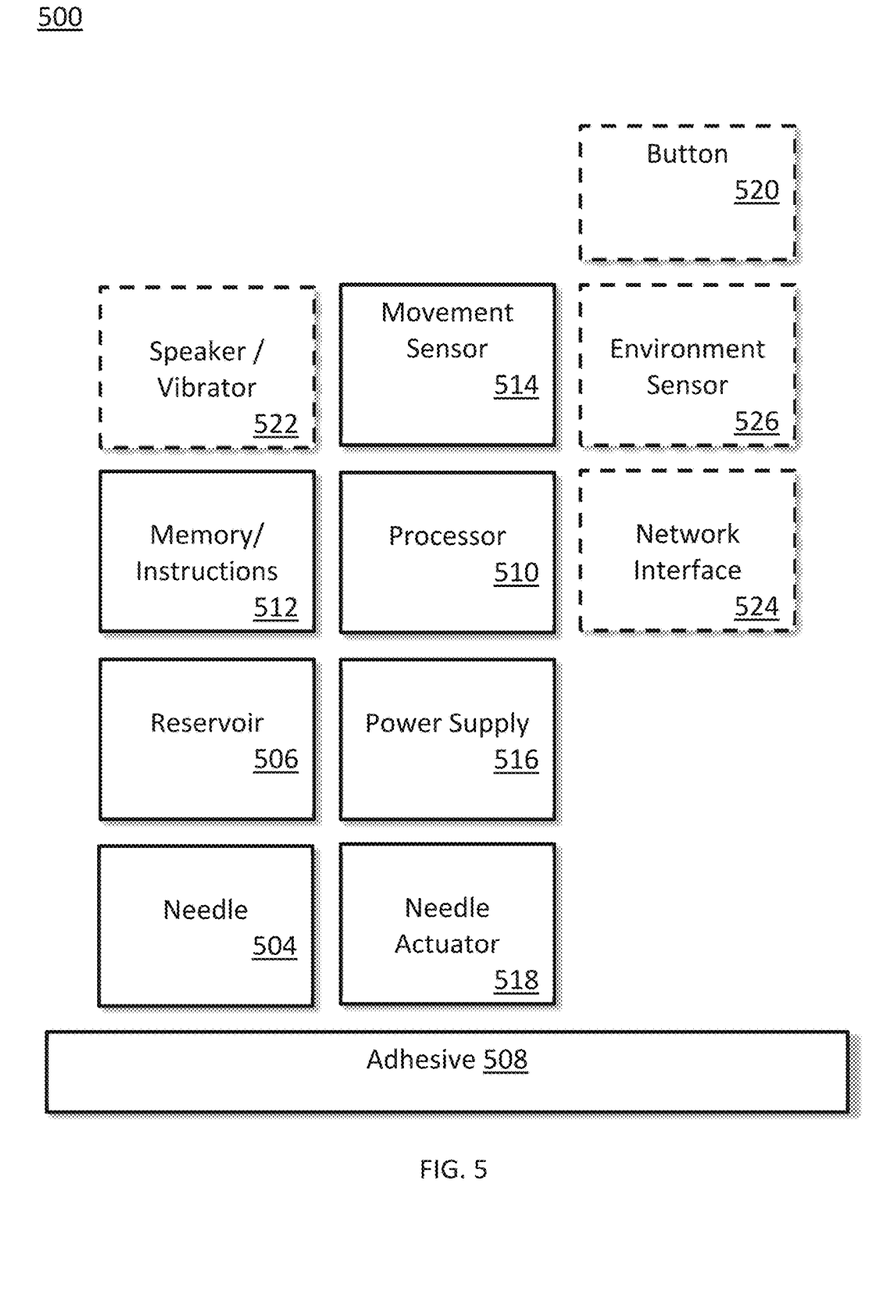
FIG. 5 is a block diagram of an exemplary medication delivery device.

FIG. 5 is a block diagram of a medication delivery device 500 in accordance with embodiments of the present invention. The medication delivery device 500 can represent an implementation of the wearable devices 100, 200, and 300 described herein. A housing 502 can include a needle 504 that can be configured to extend into the body of a wearer and dispense medication from a reservoir 506. An adhesive material or substance 508 can be attached to one side of the housing 502. The adhesive 502 may be used to attach the housing 502 to the body of a person.

A computer processor 510 may execute software instructions stored in a memory 512. The processor 510 may be, for example, a general-purpose processor, a digital-signal processor, an application specific integrated circuit (ASIC), or any other type of digital logic. The processor 510 may also or instead include analog or mixed-signal circuitry that does not require the execution of software instructions to carry out the methods described herein. The memory 512 may volatile or non-volatile and may be a random access memory (RAM), read only memory (ROM), flash memory, solid-state storage, and/or magnetic storage. The software instructions may include assembly code written directly or compiled from a higher-level language, such as C or JAVA. The computer processor 510 can be considered to be a controller for directing operations and functionality of the medication delivery device 500 overall and the constituent components thereof.

A movement sensor 514 detects movement of the housing 502 and, by extension, movement of the person to whom the housing 502 is attached. Any type of movement sensor is within the scope of the present invention, and the movement sensor 514 may detect position, velocity, acceleration, jerk, orientation, rotation, or any other similar movement type. In some embodiments, the movement sensor 514 can include three microelectromechanical systems (MEMS) capacitors oriented to capture acceleration information on x, y, and z axes. The movement sensor 514 can be in electrical communication with the processor 510 via, for example, wires or a bus. The processor 510, memory 512, and the movement sensor 514 are depicted as separate components but are not so limited. The present invention is not limited to only this arrangement of components as two or more of these components may be combined, such as in a system-on-a-chip arrangement.

A power supply 516 supplies power to the processor 510, memory 512, movement sensor 514, and/or any other components in or on the housing 502 that require power. As mentioned above, the power supply 516 may include one or more cells or batteries, which may be single-use or rechargeable. The power supply 516 may be configured to supply power to the system 500 for a certain minimum amount of time, e.g., one day, two days, or three days. The adhesive 508 may be configured or selected such that it loses some or all of its adhesive properties before this minimum power-supply time, thus prompting the person to replace the system 500 with a new one.

As mentioned above, the processor 510 can determine whether the person is having a seizure by monitoring data received from the movement sensor 514. Any method of seizure detection is within the scope of the present invention. In some embodiments, the processor 510 executes software instructions that calculate the direction, velocity, duration, and/or frequency of the person's movements and compares these factors against thresholds. If the factors exceed one or more thresholds, the processor 510 determines that the person is having a seizure or experience some other serious medical event and sends a signal to a needle actuator 518 to deploy the needle 504 and dispense the medication in the reservoir 506. In some embodiments, for example, if the processor 510 detects a certain number of rapid, back-and-forth movements made by the person within a certain period of time, the processor can determine that the person is having a seizure. The processor 510 may further detect if the person falls to the ground before, during, or after the back-and-forth movements as further evidence of a seizure.

The housing may further include devices for the input of information, such as a button 520, or the output of information, such as speaker/vibrator 522. In some embodiments, if the processor 510 detects a seizure, before signaling the needle actuator 518 to activate, the processor can determine to alert the person using the output device 522 by sounding an alarm and/or causing vibrations. In other embodiments, the output device 522 delivers heat or an electric shock to the body of the person to thereby alert the person. If the person is not having a seizure and presses the button 520 within a certain amount of time (e.g., ten seconds), the processor 510 can cancel deployment of the needle 504. In such instances, the button 520 can operate as an override or false alarm input. In some embodiments, the processor 510 adjusts one or more thresholds in response to the pressing of the button to thereby reduce or prevent false positives in the future.

The needle actuator 518 may represent the system 400 or 450 described above with reference to FIGS. 4A-4D or may be any other system for deploying the needle 504 and/or dispensing the medication in the reservoir 506. The needle 504, reservoir 506, and needle actuator 518 are depicted as separate components in this embodiment, but in other embodiments two or more of these components may be integrated together as the present invention is not limited to any particular arrangement or combination of components.

Embodiments of the present invention are not limited to only the above-described components as other components and features are within its scope. For example, a network interface 524 may be used to communicate between the system 500 and other systems, such as remote computing devices, servers, or cellular phones. For example, a remote system may transmit a message to the device 500 via any wired or wireless networking protocol, such as Wi-Fi, Ethernet, Bluetooth, NFC, or any cellular network standard, that is received using the network interface 524. The message may cause the processor 510 to automatically deploy the needle 504 and medication, cause an output device 522 to beep or vibrate, disable the device 500, or perform any other action.

An environment sensor 526 may be used instead of or in addition to the movement sensor 514. The environment sensor 526 may sample air, water, particles, or other characteristics in a surrounding environment of the device 500 for potentially harmful substances, such as sarin gas. If the environment sensor 526 detects such a substance, it sends a signal to the processor 510, which may deploy the needle 504 in response as described above.

The medication delivery device 500 may also include one or more medical condition sensors (not shown in FIG. 5). The medical condition sensors can measure characteristics of the user such as, for example, pulse rate, blood pressure, temperature, glucose levels, and oxygen levels. Separately, or in conjunction with movement sensor 514 and/or the environmental sensor 526, a medical condition sensor can send a signal to the processor 510, which may deploy the needle 504 in response to a severe medical condition being experienced by the user. In general, the medication delivery device 500 can include any number and any type of sensors including sensors for collecting information regarding one or more physical attributes of a user (e.g., motion of a user, etc.), one or more medical conditions of a user (e.g., heart rate, blood pressure, temperature, etc.), and/or one or more conditions of an environment of a user (e.g., presence of a gas or other toxin, temperature, oxygen level, etc.). Such sensors can be, for example, biosensors (e.g., for collecting biochemical data), environmental sensors, motions sensors, or a medical condition sensor.

The output device 522 can provide a visual or audible alarm to a user. For example, the output device 522 can include one or more visual device—e.g., light emitting diodes (LEDs)—for indicating an alarm. Under such a scenario, the output device 522 can flash one or more LEDs to indicate an alarm and/or can indicate an alarm by a particular color provided by one or more LEDs. The output device 522 can also include a speaker for providing an audible alarm. Further, the output device 522 can include a vibrator for vibrator all or a portion of the medication delivery device 500. As the medication delivery device 500 is directly in physical contact with a user, a vibrational alarm can be quickly detected by the user in a discrete manner. The output device 522 can be or include other components for providing an alarm including, for example, thermal actuator or electrical stimulator.

The reservoir 506 can contain one or more medications or drugs stored in one or more reservoir chambers such that the medication delivery device 500 can respond to one or more different medical events that can be experienced by a user. In various embodiments, the reservoir 506 can store is firazyr, icatibant, epinephrine, atropine, biperiden, and/or pralidoxime. In various embodiments, the medication delivery device 500 can determine a user is experiencing a severe medical event such as exposure to a chemical warfare weapon (e.g., a gas or other toxin), a seizure, an allergic reaction, and an epileptic attack (with any such condition or event caused by exposure to one or more conditions of an environment occupied by the user).

In various embodiments, the medication delivery device 500 can use one or more sensors (e.g., the sensors 514 and/or sensors 526) to sense or detect a physical attribute of a person (e.g., a motion of a user and/or a medical condition such as heart rate of a user) and/or a condition of an environment occupied by a user (e.g., a temperature of the environment and/or the presence of a chemical warfare weapon or gas or other toxin). A controller of the medication delivery device 500 (e.g., the processor 510) can use information collected and provided by the one or more sensors to determine if the user is experiencing a severe medical event. If so, the controller can direct or cause a medication to be automatically delivered to a user (e.g., by way of the needle actuator 518 in conjunction with the needle 504 and reservoir 506). The delivery of the responsive medication is intended to offset the medical event being experienced by the user. Further, the medication is provided automatically such that a user need not actively take steps to ensure delivery of the medication (e.g., to ensure delivery of the medication in situations where the user is unable or incapable of physically manipulating a medication delivery system).

Once a determination is made by the controller that a user is experiencing a medical event, the controller can provide an alarm as discussed above to the user. Within a predetermined amount of time after the determination is made and/or the alarm is provided, the controller can cause or direct the needle actuator 518 to inject the user. The predetermined amount of time (e.g., the wait time or delay time) can vary for different determined medical conditions and/or determined severity of any particular medical event. During this delay or wait time, a user can press a button 520 or other input device to cancel or prevent the automatic injection of the user. If no input is received by the medication delivery device 500 during the delay time, then injection of the user can occur at the end of the predetermined amount of time.

If a user overrides automatic injection and delivery of the medication (e.g., for a false alarm event), then the controller 510 can adjust one or more thresholds associated with detection and determination of medical events. That is, a relatively higher threshold can be required for medical events in order to trigger the automatic response. These higher thresholds could include more motion, more severe motion, more jerky motion, higher levels of detected toxins, and/or higher medical condition readings (e.g., higher heart rates, higher blood pressure) which would need to be met or exceeded before determining any subsequent medical event after false alarm reporting by the user. In essence, thresholds associated with determining instances of a medical event based on information collected by the sensors can be adjusted in response to a false reporting by a user (e.g., so as to reduce the likelihood of a false alarm event in the future). In various embodiments, any override by the user can itself be overridden based on a signal received remotely over the network interface 524. For example, an accidental cancellation of an automatic injection of the user can be overridden by remote observation and direction provide through the network interface 524.

Each of the components shown in the medication delivery device 500 can be physically and/or electrically coupled together. For example, the controller 510 can be coupled electrically to the sensors 514 and 526, the network interface 524, the button 520, the output device 522, the memory 512, and the needle actuator 518 to enable communication and/or control information, signals, and instructions to be provided therebetween. Further, the needle actuator 518 can be physically coupled to the needle 504 and the reservoir 506.

Figure 6:
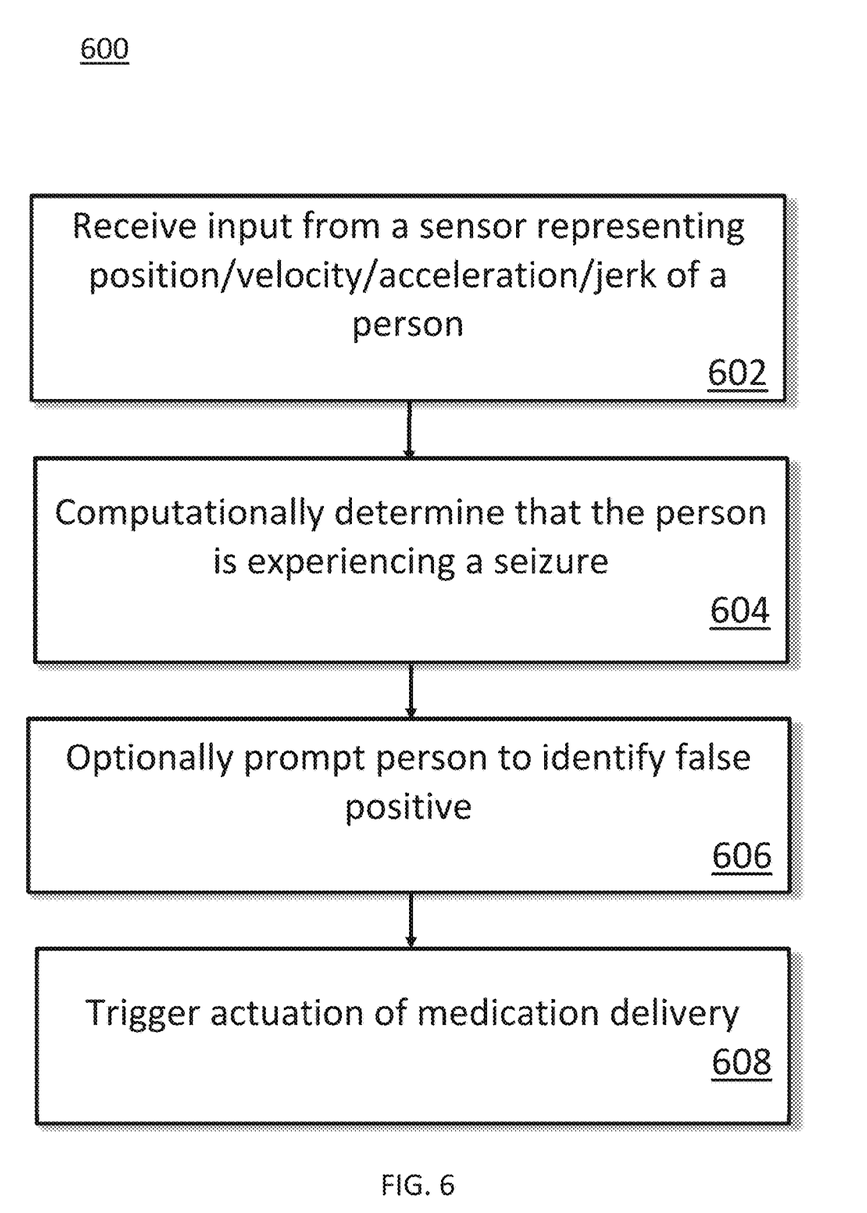
FIG. 6 illustrates a first method for delivering medication.

FIG. 6 illustrates a method 600 for delivering a medication in accordance with embodiments of the present invention. The method 600 can be implemented by the wearable devices 100, 200, and 300 described above or by the medication delivery device 500 described above. In a first step 602, input from a sensor representing a position, velocity, acceleration, or jerk of the person is received. In a second step 604, it is computationally determined that the patient is experiencing a seizure (or other severe medical event) based on the received input. In an optional third step 606, the person is prompted to identify a false positive prior to triggering mechanical actuation. In a fourth step 608, mechanical actuation of the medication delivery is triggered based on the determination.

Figure 7:
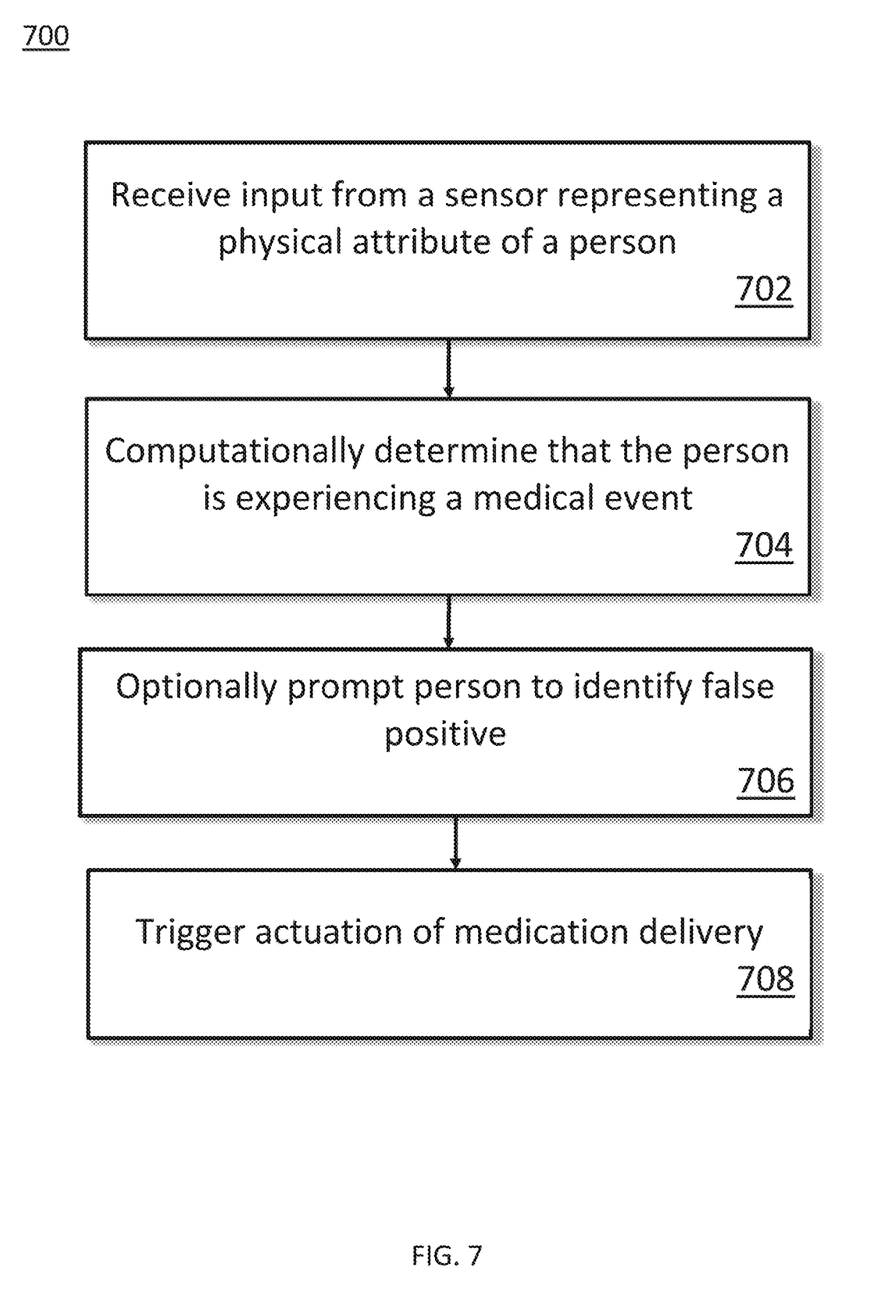
FIG. 7 illustrates a second method for delivering medication.

FIG. 7 illustrates a method 700 for delivering a medication in accordance with embodiments of the present invention. The method 700 can be implemented by the wearable devices 100, 200, and 300 described above or by the medication delivery device 500 described above. In a first step 702, input from a sensor representing a physical attribute of the person is received. In a second step 704, it is computationally determined that the patient is experiencing a medical event based on the received input. As an example, the received input can include inputs received remotely, or inputs from an environment sensor, a movement sensor, and/or a medical condition sensor. In an optional third step 706, the person is prompted to identify a false positive prior to triggering mechanical actuation. In a fourth step 708, mechanical actuation of the medication delivery is triggered based on the determination.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A wearable medication delivery device, comprising:
an environmental sensor configured to detect a condition of a surrounding environment occupied by a user based on sampling air in the surrounding environment;
a controller coupled to the environmental sensor, and configured to determine that the user is experiencing a medical event based on the condition of the surrounding environment detected by the environmental sensor;
a reservoir of medication; and
a needle actuator coupled to the reservoir and to the controller, the needle actuator configured to inject a needle into the user in response to the controller determining the user is experiencing the medical event, wherein the medication is subsequently dispensed from the reservoir to the user through the needle,
wherein the needle actuator further comprises:
a spring;
a needle driver coupled to the spring at a first end of the needle driver and coupled to the needle at a second, opposite end of the needle driver;
a first key having a first protrusion positioned in a first opening of the needle driver, the first key and the first opening positioned on a first side of the needle driver;
a second key having a second protrusion positioned in a second opening of the needle driver, the second key and the second opening positioned on a second, opposite side of the needle driver; and
an electrically deformable material disposed around the needle driver and positioned through a first hole in the first key and positioned through a second hole in the second key,
wherein:
the needle driver is under load of the spring, and the first and second keys restrict movement of the needle driver when the first protrusion is positioned in the first opening of the needle driver and the second protrusion is positioned in the second opening of the needle driver,
when the controller determines the user is experiencing the medical event, the controller is further configured to cause the electrically deformable material to change shape, and in response to the electrically deformable material changing shape, the first protrusion of the first key is released from the first opening of the needle driver and the second protrusion of the second key is released from the second opening of the needle driver, thereby allowing the spring to expand and propel the needle driver in a direction to cause the needle to inject the user.

2. The wearable medication delivery device of claim 1, further comprising a housing having an outer surface in direct physical contact with the user.

3. The wearable medication delivery device of claim 2, wherein the outer surface further comprises an adhesive for attaching the wearable medication delivery device to the user.

4. The wearable medication delivery device of claim 1, further comprising a motion sensor.

5. The wearable medication delivery device of claim 4, the motion sensor is configured to detect a motion of the user.

6. The wearable medication delivery device of claim 1, wherein the condition of the surrounding environment being a presence of a gas.

7. The wearable medication delivery device of claim 6, wherein the gas is sarin gas.

8. There wearable medication delivery device of claim 7, wherein the medical event is an exposure to a chemical warfare weapon.

9. The wearable medication delivery device of claim 1, wherein the controller is further configured to provide an alarm to the user prior to causing the needle actuator to inject the needle into the user.

10. The wearable medication delivery device of claim 9, wherein the alarm is a visual alarm.

11. The wearable medication delivery device of claim 9, wherein the alarm is an audible alarm.

12. The wearable medication delivery device of claim 9, wherein the alarm includes vibrating a portion of the wearable medication delivery device.

13. The wearable medication delivery device of claim 9, further comprising an override button, wherein the user presses the override button in response to the alarm to prevent the needle actuator from injecting the needle into the user.

14. The wearable medication delivery device of claim 1, wherein the needle driver comprises the reservoir of medication.

15. The wearable medication delivery device of claim 1, wherein the needle driver comprises a fluid conduit coupling the reservoir of medication to the needle.

16. The wearable medication delivery device of claim 1, wherein the electrically deformable material changes shape by having a diameter of the electrically deformable material increase.

17. A method of delivering a medication to a user from a wearable medication device directly attached to the user, comprising:
receiving information from an environmental sensor configured to sample air in a surrounding environment of the user;
determining the user is experiencing a medical event based on the received information from the sensor, the medical event comprising an exposure to a toxic gas;
providing an alarm to the user indicating that the user is experiencing the medical event; and
in response to the user failing to press an override button within a predetermined amount time from when the alarm is provided, injecting a needle into the user and dispensing the medication from a reservoir to the user through the needle, otherwise if the user presses the override button within the predetermined amount of time, preventing injection of the needle into the user,
wherein injecting the needle into the user includes activating a needle actuator coupled to the needle, wherein the needle actuator comprises:
a spring;
a needle driver coupled to the spring at a first end of the needle driver and coupled to the needle at a second, opposite end of the needle driver;
a first key having a first protrusion positioned in a first opening of the needle driver, the first key and the first opening positioned on a first side of the needle driver;
a second key having a second protrusion positioned in a second opening of the needle driver, the second key and the second opening positioned on a second, opposite side of the needle driver; and
an electrically deformable material disposed around the needle driver and positioned through a first hole in the first key and positioned through a second hole in the second key,
wherein:
the needle driver is under load of the spring, and the first and second keys are configured to restrict movement of the needle driver when the first protrusion is positioned in the first opening of the needle driver and the second protrusion is positioned in the second opening of the needle driver,
when the controller determines the user is experiencing the medical event the controller causes the electrically deformable material to change shape, and
in response to the electrically deformable material changing shape, the first protrusion of the first key is released from the first opening of the needle driver and the second protrusion of the second key is released from the second opening of the needle driver, thereby allowing the spring to expand and to propel the needle driver in a direction to cause the needle to inject the user.

18. The method of claim 17, wherein the toxic gas is sarin gas.

19. The method of claim 17, further comprising receiving medical condition information of the user from a medical condition sensor.

20. The method of claim 17, further comprising receiving motion information of the user from a motion sensor.

* * * * *